United States Patent
Kwon et al.

(10) Patent No.: US 9,512,353 B2
(45) Date of Patent: Dec. 6, 2016

(54) COMPOSITION COMPRISING QUANTUM DOT AND DEVICE USING SAME

(71) Applicant: LMS CO., LTD, Pyeongtaek-si (KR)

(72) Inventors: Doo Hyo Kwon, Anyang-si (KR); Jeong Og Choi, Seoul (KR); Myeon Choeon Choi, Anyang-si (KR)

(73) Assignee: LMS Co., Ltd., Pyeongtaek-si (KR)

( * ) Notice: Subject to any disclaimer, the term of this patent is extended or adjusted under 35 U.S.C. 154(b) by 208 days.

(21) Appl. No.: 14/374,062

(22) PCT Filed: Feb. 1, 2013

(86) PCT No.: PCT/KR2013/000818
§ 371 (c)(1),
(2) Date: Oct. 2, 2014

(87) PCT Pub. No.: WO2013/115589
PCT Pub. Date: Aug. 8, 2013

(65) Prior Publication Data
US 2015/0034875 A1 Feb. 5, 2015

(30) Foreign Application Priority Data

Feb. 1, 2012 (KR) .................. 10-2012-0010362

(51) Int. Cl.
C07F 7/18 (2006.01)
C09K 11/00 (2006.01)
H01L 51/50 (2006.01)
C09K 11/02 (2006.01)
C09K 11/88 (2006.01)
H01L 33/50 (2010.01)

(52) U.S. Cl.
CPC ............ *C09K 11/025* (2013.01); *C07F 7/1852* (2013.01); *C09K 11/02* (2013.01); *C09K 11/883* (2013.01); *H01L 33/501* (2013.01)

(58) Field of Classification Search
CPC ..................................................... C09K 11/025
See application file for complete search history.

(56) References Cited

U.S. PATENT DOCUMENTS

| | | | |
|---|---|---|---|
| 7,192,795 B2 * | 3/2007 | Boardman | H01L 33/52 257/E23.119 |
| 7,199,393 B2 | 4/2007 | Park et al. | |
| 7,476,487 B2 | 1/2009 | Park et al. | |
| 2009/0146175 A1 * | 6/2009 | Bahadur | H01L 33/56 257/100 |
| 2011/0240931 A1 | 10/2011 | Jang et al. | |
| 2012/0168815 A1 * | 7/2012 | Koh | C08L 83/04 257/100 |

FOREIGN PATENT DOCUMENTS

| | | |
|---|---|---|
| KR | 1020050038120 A | 4/2005 |
| KR | 1020070089163 A | 8/2007 |
| KR | 1020110110669 A | 10/2011 |

\* cited by examiner

*Primary Examiner* — Carol M Koslow
(74) *Attorney, Agent, or Firm* — The Webb Law Firm

(57) ABSTRACT

The present invention provides a composition including a quantum dot and vinyl siloxane including an alkyl group having a carbon number of 4 or more, and a device to which the composition is applied, wherein the composition can effectively be applied to various types of light emitting devices due to excellent dispersibility of quantum dots, UV-stability, and heat-resistance.

18 Claims, 1 Drawing Sheet

COMPOSITION COMPRISING QUANTUM DOT AND DEVICE USING SAME

CROSS-REFERENCE TO RELATED APPLICATIONS

This application is the United States national phase of International Application No. PCT/KR2013/000818 filed Feb. 1, 2013, and claims priority to Korean Patent Application No. 10-2012-0010362 filed Feb. 1, 2012, the disclosures of which are hereby incorporated in their entirety by reference.

BACKGROUND

1. Field of the Invention

A composition including vinyl siloxane and a quantum dot, and various fields of application of the composition are included.

2. Discussion of Related Art

A quantum dot is a material having a crystalline structure of only a few nanometers in size, and is composed of about several hundred atoms to several thousand atoms. Since the quantum dot is very small, a quantum confinement effect occurs therein. The quantum confinement effect refers to a phenomenon in which when an object is reduced to a nano size or less, an energy band gap of the object is increased. Accordingly, when light of a wavelength having energy higher than the energy band gap is incident onto the quantum dot, the quantum dot absorbs the light so that an energy level of the quantum dot changes to an excited state, and then the energy level of the quantum dot drops to a ground state while the quantum dot emits light having a specific wavelength. The wavelength of the emitted light is determined by an energy corresponding to the band gap.

In general, the smaller the particle of a quantum dot is, the shorter the wavelength of light that is generated is, and the larger the particle of the quantum dot is, the longer the wavelength of light that is generated is. This is a distinct electrical and optical property different from that of existing semiconductor materials. Therefore, the light emitting characteristics of the quantum dot that are desired may be implemented by controlling the size, composition and the like of the quantum dot.

SUMMARY OF THE INVENTION

1. Technical Problem

The present invention provides a composition comprising a quantum dot and vinyl siloxane including an alkyl group having a carbon number of 4 or more, a cured material of the composition, and a device using the same.

2. Technical Solution

In an exemplary embodiment, the present invention provides a composition comprising a quantum dot and vinyl siloxane including an alkyl group having a carbon number of 4 or more.

The vinyl siloxane may have a structure of the following Chemical Formula 1.

[Chemical Formula 1]

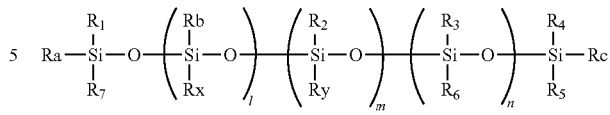

In Chemical Formula 1,

Ra, Rb, and Rc are independently an alkyl group having a carbon number of 1 to 4, a vinyl group, or an aryl group having a carbon number of 6 to 18, and one or more of Ra, Rb, and Rc are a vinyl group, $R_1$ to $R_7$ are independently an alkyl group having a carbon number of 1 to 4, or an aryl group having a carbon number of 6 to 18, Rx and Ry are independently an alkyl group having a carbon number of 1 to 3, an alkyl group having a carbon number of 4 to 20, or an aryl group having a carbon number of 6 to 18, and one or more of Rx and Ry are an alkyl group having a carbon number of 4 to 20, and l, m, and n are numbers which satisfy a ratio of 0.02 to 0.4:0.02 to 0.4:0.2 to 0.96 (l:m:n).

Further, the present invention provides a cured material of the composition and a device using the cured material.

3. Effect of the Invention

The cured material of the composition according to the present invention can be effectively applied to various types of devices due to excellent quantum yield, heat-resistance, and UV stabilization properties.

BEST MODE

Figure 1:
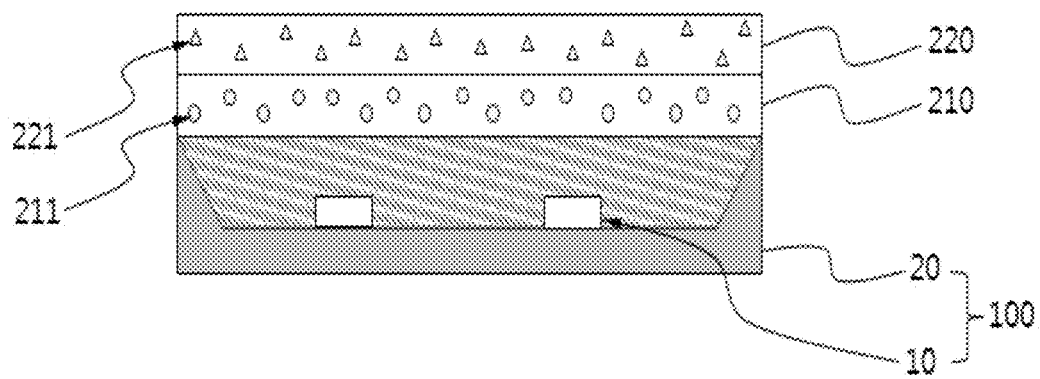
FIGS. 1 to 3 each schematically illustrate an LED device to which a cured material of the composition according to an exemplary embodiment of the present invention is applied.

Hereinafter, the present invention will be described in more detail.

In the present invention, vinyl siloxane is meant to include all of the following: a monomer, an oligomer, a polymer, a copolymer, and the like.

In the present invention, vinyl siloxane has a structure which includes a vinyl group bonded to a basic framework of siloxane. In some cases, the vinyl siloxane may be a monofunctional or polyfunctional vinyl siloxane. The monofunctional vinyl siloxane refers to a vinyl siloxane having a structure in which one functional group is bonded to a vinyl siloxane structure, and the polyfunctional vinyl siloxane refers to vinyl siloxane in which two or more functional groups are bonded to vinyl siloxane structure. For example, the polyfunctional vinyl siloxane may be selected from difunctional vinyl siloxane, a trifunctional vinyl siloxane, tetrafunctional vinyl siloxane, or a mixture of the vinyl siloxanes, and the like.

In addition, the vinyl siloxane may be vinyl siloxane including an alkyl group having a carbon number of 4 or more. The alkyl group having a carbon number of 4 or more is not particularly limited as long as the alkyl group has a carbon number of 4 or more, and includes both straight-chain or branched-chain structures. For example, the alkyl group having a carbon number of 4 or more may be an alkyl group having a carbon number of 4 to 30, an alkyl group having a carbon number of 4 to 20, or an alkyl group having a carbon number of 4 to 12.

The structures of the vinyl siloxanes illustrated in the following chemical formulas may have the structures of a polymer as well as a monomer. Accordingly, a, b, l, m, n, p, q, and the like may be expressed as a constant ratio.
Hereinafter, the molecular weight in the present invention refers to a weight average molecular weight calculated in terms of polystyrene.

The composition according to the present invention may be a composition comprising a quantum dot and vinyl siloxane including an alkyl group having a carbon number of 4 or more. The quantum dot has a core/shell structure and may be a nanocrystal of a Group II-VI compound semiconductor such as CdS, CdSe, CdTe, ZnS, ZnSe, ZnTe, HgS, HgSe, and HgTe, a nanocrystal of a Group III-V compound semiconductor such as GaN, GaP, GaAs, InP, and InAs, or a mixture thereof. The quantum dot composed of a core/shell structure generally has hydrophobic properties due to receiving surface treatment with an alkyl chain having a carbon number of 6 to 30. When vinyl siloxane is used in related art, the vinyl siloxane usually includes a methyl group or a phenyl group, so that there is a problem in that compatibility with a hydrophobic quantum dot, which generally includes an alkyl chain having a carbon number of 6 to 30 on the surface thereof, decreases. The decrease in compatibility of a polymer matrix of the vinyl siloxane with the quantum dot causes quenching due to the aggregation of nano-sized quantum dots, and as a result, a decrease in quantum yield occurs. In order to solve the problem, vinyl siloxane including an alkyl group having a carbon number of 4 or more is used in the present invention. By using vinyl siloxane substituted with an alkyl group having a carbon number of 4 or more, a hydrophobic quantum dot including an alkyl chain having a carbon number of 6 to 30 on the surface thereof can be uniformly dispersed in a matrix of the vinyl siloxane, and the dispersion stability can be enhanced during storage over a long period of time. A cured material prepared with the composition which is excellent in dispersibility can enhance quantum yield, optical transmittance, heat resistance, and UV-stability.

In an exemplary embodiment, the vinyl siloxane including an alkyl group having a carbon number of 4 or more may include a structure of the following Chemical Formula 1.

[Chemical Formula 1]

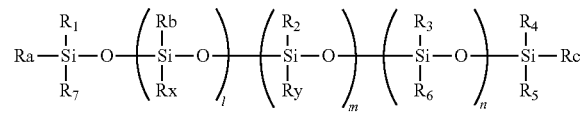

In Chemical Formula 1,
Ra, Rb, and Rc are independently an alkyl group having a carbon number of 1 to 4, a vinyl group, or an aryl group having a carbon number of 6 to 18, and one or more of Ra, Rb, and Rc are a vinyl group,
$R_1$ to $R_7$ are independently an alkyl group having a carbon number of 1 to 4, or an aryl group having a carbon number of 6 to 18,
Rx and Ry are independently an alkyl group having a carbon number of 1 to 3, an alkyl group having a carbon number of 4 to 20, or an aryl group having a carbon number of 6 to 18, and one or more of Rx and Ry are an alkyl group having a carbon number of 4 to 20, and l, m, and n are numbers which satisfy a ratio of 0.02 to 0.4:0.02 to 0.4:0.2 to 0.96 (l:m:n).
Specifically, in the definition of Chemical Formula 1,
Ra, Rb, and Rc are independently a methyl group, a vinyl group, or a phenyl group, and one or more of Ra, Rb, and Rc are a vinyl group,
$R_1$ to $R_7$ are independently a methyl group or a phenyl group,
Rx and Ry are independently a methyl group, an alkyl group having a carbon number of 4 to 20, or a phenyl group, and one or more of Rx and Ry are an alkyl group having a carbon number of 4 to 20, and
l, m, and n may satisfy a ratio of 0.02 to 0.3:0.02 to 0.3:0.4 to 0.96 (l:m:n).

In another exemplary embodiment, the vinyl siloxane including an alkyl group having a carbon number of 4 or more may include a structure of the following Chemical Formula 2.

[Chemical Formula 2]

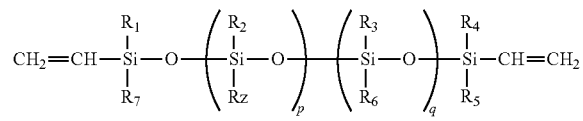

In Chemical Formula 2,
$R_1$ to $R_7$ are independently an alkyl group having a carbon number of 1 to 4, or an aryl group having a carbon number of 6 to 18,
Rz is an alkyl group having a carbon number of 4 to 20, and
p and q are numbers which satisfy a ratio of 0.04 to 0.8:0.2 to 0.96 (p:q).
Specifically, in the definition of Chemical Formula 2,
$R_1$ to $R_7$ are independently a methyl group or a phenyl group,
Rz is an alkyl group having a carbon number of 4 to 20, and
p and q may satisfy a ratio of 0.04 to 0.4:0.6 to 0.96 (p:q).

In yet another exemplary embodiment, the vinyl siloxane including an alkyl group having a carbon number of 4 or more may include a structure of the following Chemical Formula 3.

[Chemical Formula 3]

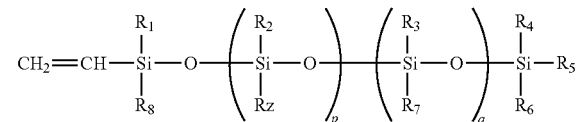

In Chemical Formula 3,
$R_1$ to $R_8$ are independently an alkyl group having a carbon number of 1 to 4, or an aryl group having a carbon number of 6 to 18,
Rz is an alkyl group having a carbon number of 4 to 20, and
p and q are numbers which satisfy a ratio of 0.04 to 0.8:0.2 to 0.96 (p:q).

Specifically, in Chemical Formula 3, $R_1$ to $R_8$ are independently a methyl group or a phenyl group, Rz is an alkyl group having a carbon number of 4 to 20, and p and q may satisfy a ratio of 0.04 to 0.4:0.6 to 0.96 (p:q).

The aforementioned vinyl siloxane including an alkyl group having a carbon number of 4 or more may include, for example, one or more of the following Chemical Formulas 4 to 7.

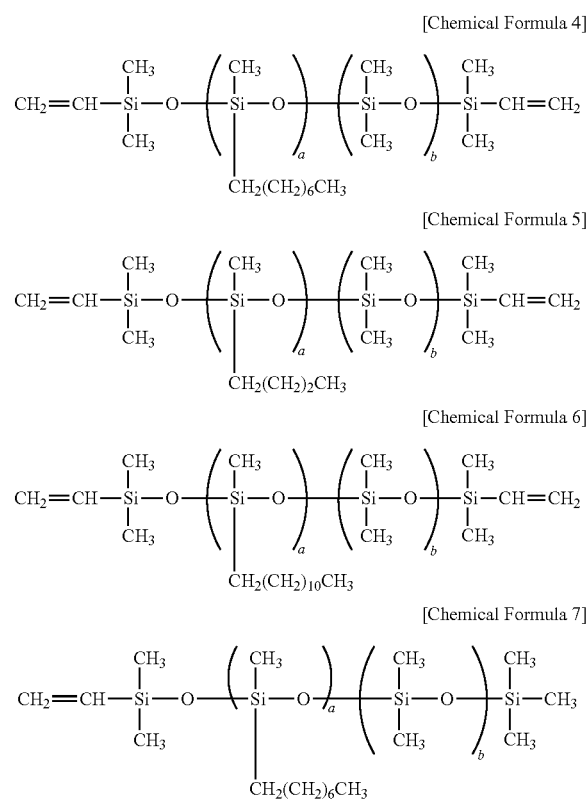

In Formulas 4 to 7, a and b independently satisfy 0.2 to 0.5:0.5 to 0.8 (a:b). For example, in Formulas 4 to 7, a and b may independently satisfy a ratio of 0.28 to 0.38:0.62 to 0.72 (a:b), or 0.35:0.65 (a:b).

The molecular weight of the vinyl siloxane used in the present invention is not particularly limited, and may have a molecular weight in a range of 300 to 50,000, 300 to 20,000, 5,000 to 35,000, or 20,000 to 30,000. In the said ranges, the composition exhibits stable dispersibility, and the quantum yield, optical transmittance, heat resistance, and UV-stability for a cured material of the composition can be improved.

As an example, the composition according to the present invention may further include vinyl siloxane including an alkyl group having a carbon number of 3 or less. For example, the vinyl siloxane including an alkyl group having a carbon number of 3 or less may include a structure of the following Chemical Formula 8.

[Chemical Formula 8]

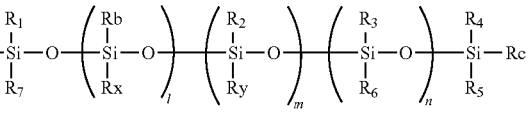

In Chemical Formula 8,

Ra, Rb, and Rc are independently an alkyl group having a carbon number of 1 to 3, a vinyl group, or an aryl group having a carbon number of 6 to 18, and one or more of Ra, Rb, and Rc are a vinyl group, $R_1$ to $R_7$ are independently an alkyl group having a carbon number of 1 to 3, or an aryl group having a carbon number of 6 to 18, Rx and Ry are independently an alkyl group having a carbon number of 1 to 3, or an aryl group having a carbon number of 6 to 18, and one or more of Rx and Ry are an alkyl group having a carbon number of 1 to 3, and l, m, and n are numbers which satisfy a ratio of 0.02 to 0.4:0.02 to 0.4:0.2 to 0.96 (l:m:n).

Specifically, in Chemical Formula 8,

Ra, Rb, and Rc are independently a methyl group, a vinyl group, or a phenyl group, and one or more of Ra, Rb, and Rc are a vinyl group, $R_1$ to $R_7$ are independently a methyl group or a phenyl group, Rx and Ry are independently a methyl group or a phenyl group, and one or more of Rx and Ry are a methyl group, and l, m, and n may satisfy a ratio of 0.05 to 0.4:0.05 to 0.4:0.2 to 0.9 (l:m:n).

Furthermore, the content of the vinyl siloxane including an alkyl group having a carbon number of 3 or less may be in a range of 20 to 3,000 parts by weight, 20 to 2,000 parts by weight, 50 to 2,500 parts by weight, or 100 to 2,000 parts by weight, with respect to 100 parts by weight of vinyl siloxane including an alkyl group having a carbon number of 4 or more.

The composition according to the present invention may include a quantum dot which is dispersed in vinyl siloxane. The type of quantum dot is not particularly limited in type, as long as the quantum dot is dispersed in vinyl siloxane including an alkyl group having a carbon number of 4 or more.

As an example, the quantum dot may have an emission peak at one or more of a wavelength of 520 to 570 nm and a wavelength of 620 to 670 nm. This includes the case in which the quantum dot emits a green and/or red light. For example, the quantum dot absorbs light from a blue LED chip or a blue light emitting fluorescent substance in order to emit a green and/or red light. As another example, the quantum dot may have an emission peak at a wavelength of 570 to 620 nm. This means that the quantum dot absorbs light from a blue LED chip or a blue light emitting fluorescent substance in order to emit a yellow light.

The content of the quantum dot may be 0.001 to 10 parts by weight, 0.001 to 5 parts by weight, 0.005 to 10 parts by weight, 0.005 to 5 parts by weight, or 0.005 to 1 part by weight, with respect to 100 parts by weight of the vinyl siloxane including an alkyl group having a carbon number of 4 or more. In the said content ranges of the quantum dot, excellent color rendering can be obtained.

The composition may further include a fluorescent substance. For example, the composition includes all of the following: a structure in which the quantum dot and the fluorescent substance are dispersed together in the vinyl siloxane, or a structure where a layer in which the fluorescent substance is dispersed is separately formed. By using the quantum dot and the fluorescent substance together, excellent quantum yield and color rendering can be obtained at the same time. The type of the fluorescent substance is not particularly limited, and includes various types of fluorescent substances commercially available in the art.

The composition according to the present invention further includes a cross-linking agent and a catalyst. Further, the composition may further include various types of additives used in the art, and the type of additive is not particularly limited.

As an example, the cross-linking agent can be represented by a structure of Chemical Formula 9.

[Chemical Formula 9]

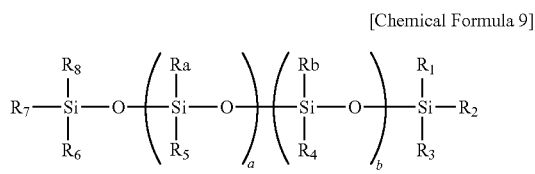

In Chemical Formula 9,

Ra and Rb are independently hydrogen, an alkyl group having a carbon number of 1 to 4, or a phenyl group, and one or more of Ra and Rb are hydrogen, $R_1$ to $R_7$ are independently an alkyl group having a carbon number of 1 to 4, or a phenyl group, and a and b are numbers which satisfy 0.002 to 0.95:0.05 to 0.998 (a:b).

In addition, the type of catalyst is not particularly limited, and a thermosetting catalyst may be used. For example, a platinum (Pt)-based catalyst may be used.

The content of the cross-linking agent and the catalyst may vary depending on the degree of cross-linking or the degree of curing which is commonly used in the art.

For example, the composition according to the present invention may include: 5 to 60 parts by weight of a cross-linking agent; and 0.01 to 0.5 part by weight of a catalyst, with respect to 100 parts by weight of vinyl siloxane including an alkyl group having a carbon number of 4 or more.

The present invention provides a cured material of the composition previously described. The method of forming the cured material is not particularly limited. For example, the composition may be cured by irradiating the composition with light such as UV light, or adding heat thereto.

The cured material may be composed in various forms. For example, the cured material may be in the form of a film or a coating.

The cured material may provide a structure in which a quantum dot is dispersed in a matrix structure which vinyl siloxane polymer forms. For example, the cured material may have a form in which a quantum dot is dispersed in a matrix structure which vinyl siloxane polymer forms.

Furthermore, the present invention provides a device including the cured material of the composition previously described. The scope of the device is not particularly limited, and may be, for example, a lighting device, or a display device.

Hereinafter, the present invention will be described in more detail through the drawings, but the scope of the present invention is not limited thereto.

Figure 2:
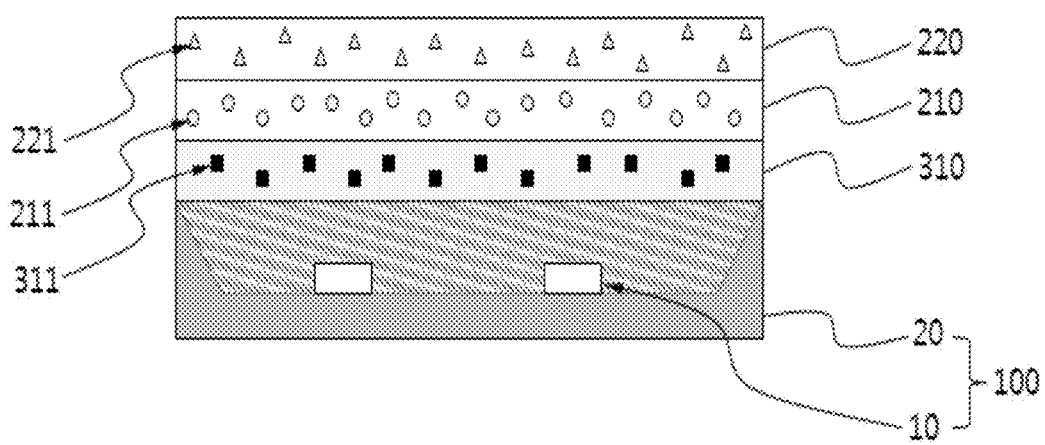
Figure 3:
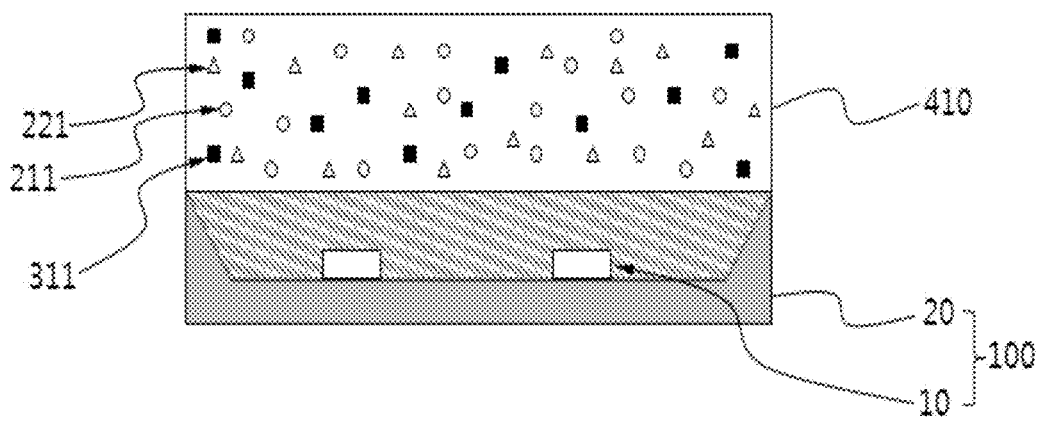

FIGS. 1 to 3 each illustrate an LED device to which a cured material of the composition according to an exemplary embodiment of the present invention is applied.

An LED device illustrated in FIG. 1 includes an LED element unit 100, and a first cured material layer 210 and a second cured material layer 220 which are formed on the LED element unit 100, which both include quantum dots. The LED element unit 100 includes a base part 20 and an LED chip 10 formed in a groove part of the base part 20. The first cured material layer 210 includes a green quantum dot 211 dispersed in a matrix structure which vinyl siloxane polymer forms. The second cured material layer 220 includes a red quantum dot 221 dispersed in a matrix structure which vinyl siloxane polymer forms. The green quantum dot 211 refers to a quantum dot having an emission peak at 520 to 570 nm, which is a green wavelength region, and the red quantum dot 221 refers to a quantum dot having an emission peak at 620 to 670 nm, which is a red wavelength region. Further, the LED chip 10 included in the LED element unit 100 is a blue LED chip, and may have an emission peak at 400 to 450 nm An LED device illustrated in FIG. 2 includes an LED element unit 100, a first cured material layer 210 and a second cured material layer 220 which are formed on the LED element unit 100, which both include quantum dots, and a third layer 310 including a fluorescent substance. The first cured material layer 210 includes a green quantum dot 211 dispersed in a matrix structure which vinyl siloxane polymer forms. The second cured material layer 220 includes a red quantum dot 221 dispersed in a matrix structure which vinyl siloxane polymer forms. In addition, the third layer 310 may include a fluorescent substance 311 which may compensate for the light emission of the green quantum dot 211 and/or the red quantum dot 221. The type of fluorescent substance may be, for example, a fluorescent substance having an emission peak at 520 to 570 nm, which is a green region, and/or 620 to 670 nm, which is a red region.

An LED device illustrated in FIG. 3 includes an LED element unit 100, and a cured material layer 410 which is formed on the LED element unit 100 and includes both a quantum dot and a fluorescent substance. The layer 410 has a structure which includes a green quantum dot 211, a red quantum dot 221, and a fluorescent substance 311, which are dispersed in a matrix structure which vinyl siloxane polymer forms.

Hereinafter, the present invention will be described in more detail through the Examples and the like. The Examples and the like of the present invention are provided only to give a detailed description of the invention, and the scope of the rights is not limited thereby.

Comparative Examples 1 and 2 and Examples 1 to 9

A composition was prepared by mixing components at the weight ratio described in the following Table 1.

Chemical Formulas 11 to 16 represent a structure of vinyl siloxane used in each of the Comparative Examples and the Examples and the like, and inside the parenthesis is provided a carbon number of alkyl groups with which each vinyl siloxane is substituted, or a phenyl group.

Hydrosiloxane having a structure of the following Chemical Formula 10 was used as the cross-linking agent.

[Chemical Formula 10]

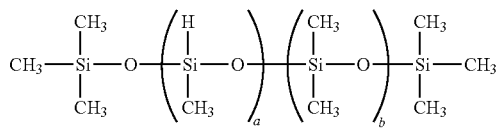

In Chemical Formula 10, a and b is 0.3:0.7, and the molecular weight thereof is 2,800.

Furthermore, a CdSe-based red quantum dot (trade name: Nanodot-HE-632) manufactured by QD Solution, Korea was used as the quantum dot, and a platinum (Pt) catalyst (trade name: SIP 6829.2) manufactured by Gelest, Inc., USA was used as the catalyst. The composition obtained by mixing each component was coated so that there was a thickness of 30 μm of the composition coated on a glass substrate, and then cured at 60° C. for 2 hours to prepare a product in the form of a film.

In Chemical Formula 12, a and b have a ratio of 0.45:0.55, and the molecular weight thereof is 7,600.

[Chemical Formula 13]

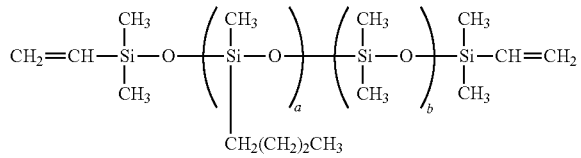

In Chemical Formula 13, a and b are a ratio of 0.35:0.65, and the molecular weight thereof is 6,500.

TABLE 1

| Classification | Chemical Formula 11 (C1) | Chemical Formula 12 (phenyl) | Chemical Formula 13 (C4) | Chemical Formula 14 (C8) | Chemical Formula 15 (C8) | Chemical Formula 16 (C12) | Crosslinking agent | Catalyst | Quantum dot |
|---|---|---|---|---|---|---|---|---|---|
| Comparative Example 1 | 80 | — | — | — | — | — | 20 | 0.1 | 0.01 |
| Comparative Example 2 | — | 80 | — | — | — | — | 20 | 0.1 | 0.01 |
| Example 1 | — | — | 80 | — | — | — | 20 | 0.1 | 0.01 |
| Example 2 | — | — | — | — | 80 | — | 20 | 0.1 | 0.01 |
| Example 3 | — | — | — | — | — | 80 | 20 | 0.1 | 0.01 |
| Example 4 | 60 | — | — | — | 20 | — | 20 | 0.1 | 0.01 |
| Example 5 | 40 | — | — | — | 40 | — | 20 | 0.1 | 0.01 |
| Example 6 | 20 | — | — | — | 60 | — | 20 | 0.1 | 0.01 |
| Example 7 | 60 | — | — | 20 | — | — | 20 | 0.1 | 0.01 |
| Example 8 | 40 | — | — | 40 | — | — | 20 | 0.1 | 0.01 |
| Example 9 | 20 | — | — | 60 | — | — | 20 | 0.1 | 0.01 |

In Table 1, the structures of Chemical Formulas 11 to 16 respectively are as follows.

[Chemical Formula 11]

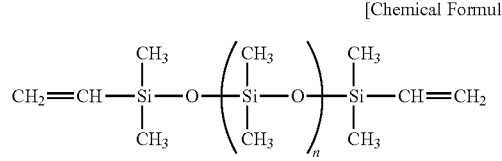

The molecular weight of Chemical Formula 11 is 8,300.

[Chemical Formula 14]

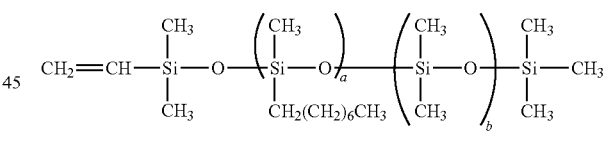

In Chemical Formula 14, a and b are a ratio of 0.35:0.65, and the molecular weight thereof is 3,600.

[Chemical Formula 12]

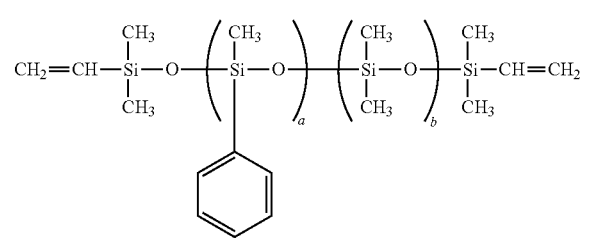

[Chemical Formula 15]

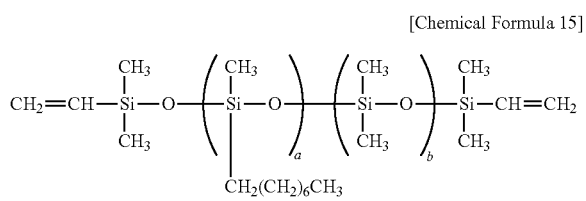

In Chemical Formula 15, a and b are a ratio of 0.35:0.65, and the molecular weight thereof is 6,500.

[Chemical Formula 16]

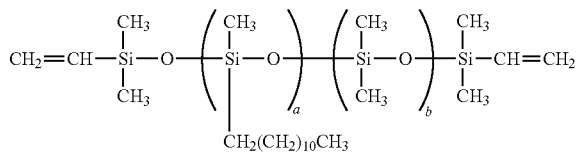

In Chemical Formula 16, a and b are a ratio of 0.45:0.55, and the molecular weight thereof is 6,500.

DETAILED DESCRIPTION OF EXEMPLARY EMBODIMENTS

Hereinafter, the present invention will be described in further detail with reference to the following Examples. It should be understood that the descriptions proposed herein are merely preferable examples for the purpose of illustration only, and not intended to limit the scope of the invention.

Experimental Example 1

Measurement of Quantum Yield (QY) and Optical Transmittance

For the films prepared according to Comparative Examples 1 and 2 and Examples 1 to 9, the quantum yield (QY) and the optical transmittance were each measured. The quantum yield was measured using an absolute quantum yield meter (trade name: C9920-02) manufactured by Hamamatsu, Inc., of Japan. And, the optical transmittance was measured using a transmittance measuring device (trade name: Cary-4000) manufactured by Agilent, Inc., USA, //and the optical transmittance refers to an average optical transmittance at a wavelength of 400 nm to 700 nm. The measurement results are provided in the following Table 2.

TABLE 2

| Classification | Quantum Yield (QY) (%) | Optical Transmittance (%) |
| --- | --- | --- |
| Comparative Example 1 | 50 | 66 |
| Comparative Example 2 | 48 | 65 |
| Example 1 | 69 | 84 |
| Example 2 | 74 | 87 |
| Example 3 | 80 | 89 |
| Example 4 | 62 | 71 |
| Example 5 | 66 | 75 |
| Example 6 | 68 | 77 |
| Example 7 | 61 | 70 |
| Example 8 | 65 | 76 |
| Example 9 | 69 | 78 |

Referring to Table 2, it can be seen that the quantum yield was 61% or more in the Examples, whereas the quantum yield was 50% or less in the Comparative Examples. According to Table 2, the film according to the present invention is excellent in regards to quantum yield, and thus can be applied to optical devices which require high luminance intensity.

Further, it can be seen that the optical transmittance of the Examples was 70% or more, whereas the optical transmittance of the Comparative Examples failed to exceed 66%. Accordingly, the film according to the present invention is excellent in regards to optical transmittance, and thus can be applied to optical devices which require transparency.

Experimental Example 2

Measurement of UV-Stability and Heat Resistance

For the films prepared according to Comparative Examples 1 and 2 and Examples 1 to 9, the UV-stability and heat resistance were measured and compared. Specifically, in regards to the UV-stability, the quantum yield ($QY_{T1}$) of the film that was prepared was measured, an ultraviolet (UV) light having a wavelength of 365 nm was irradiated at a power of about 1 mW/cm² for about 48 hours, that is, under a harsh condition of about 173 J/cm², and then the quantum yield ($QY_{T2}$) was measured again to calculate the change in quantum yield ($\Delta QY = QY_{T1} - QY_{T2}$, %). In addition, for the heat resistance experiment, the quantum yield ($QY_{U1}$) for the film that was prepared was measured, the film was exposed at 90° C. for 240 hours, and then the quantum yield ($QY_{U2}$) was measured again to calculate the difference in quantum yield ($\Delta QY = QY_{U1} - QY_{U2}$, %). The results of the experiment are provided in the following Table 3.

TABLE 3

| Classification | UV-Stability ($\Delta QY$, %) (UV irradiation, 48 hr) | Heat Resistance ($\Delta QY$, %) (90° C., 240 hr) |
| --- | --- | --- |
| Comparative Example 1 | 32 | 21 |
| Comparative Example 2 | 28 | 23 |
| Example 1 | 8 | 8 |
| Example 2 | 6 | 6 |
| Example 3 | 4 | 5 |
| Example 4 | 12 | 11 |
| Example 5 | 11 | 9 |
| Example 6 | 10 | 9 |
| Example 7 | 11 | 10 |
| Example 8 | 10 | 9 |
| Example 9 | 10 | 8 |

Referring to Table 3, it can be seen that in the Examples, $\Delta QY$ does not exceed 12% in terms of UV-stability. However, it can be seen that in the Comparative Examples, $\Delta QY$ which measures UV-stability was measured was 28% or more. According to Table 3, the film according to the present invention was relatively excellent in regards to UV-stability, and thus is advantageous in the application of optical devices which require exposure of UV light (internal light), which is generated from an LED itself for a long period of time, and solar light (external light).

Furthermore, it can be seen that in the Examples, $\Delta QY$ does not exceed 11% in terms of heat resistance. However, it can be seen that in the Comparative Examples, $\Delta QY$ which measures heat resistance was 21% or more. Thus, the film according to the present invention has excellent heat resistance, and thus maintains stable characteristics in regards to high heat generated from a white LED when applied to the LED.

What is claimed is:
1. A composition comprising vinyl siloxane including an alkyl group having a carbon number of 4 or more and a quantum dot,
   wherein the vinyl siloxane comprises a structure of the following Chemical Formula 1:

[Chemical Formula 1]

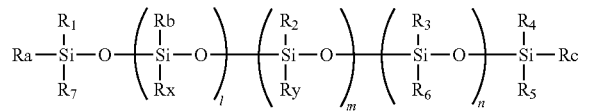

in Chemical Formula 1,

Ra, Rb, and Rc are independently an alkyl group having a carbon number of 1 to 4, a vinyl group, or an aryl group having a carbon number of 6 to 18, and one or more of Ra, Rb, and Rc are a vinyl group, $R_1$ to $R_7$ are independently an alkyl group having a carbon number of 1 to 4, or an aryl group having a carbon number of 6 to 18, Rx and Ry are independently an alkyl group having a carbon number of 1 to 3, an alkyl group having a carbon number of 4 to 20, or an aryl group having a carbon number of 6 to 18, and one or more of Rx and Ry are an alkyl group having a carbon number of 4 to 20, and l, m, and n are numbers which satisfy a ratio of 0.02 to 0.4:0.02 to 0.4:0.2 to 0.96 (l:m:n).

2. The composition of claim 1, wherein the vinyl siloxane comprises a structure of the following Chemical Formula 2:

[Chemical Formula 2]

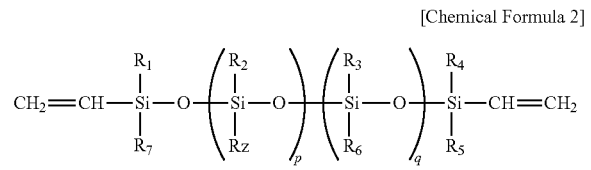

in Chemical Formula 2, $R_1$ to $R_7$ are independently an alkyl group having a carbon number of 1 to 4, or an aryl group having a carbon number of 6 to 18, Rz is an alkyl group having a carbon number of 4 to 20, and p and q are numbers which satisfy a ratio of 0.04 to 0.8:0.2 to 0.96 (p:q).

3. The composition of claim 1, wherein the vinyl siloxane comprises a structure of the following Chemical Formula 3:

[Chemical Formula 3]

$$CH_2{=}CH-\underset{\underset{R_7}{|}}{\overset{\overset{R_1}{|}}{Si}}-O{\left(\underset{\underset{Rz}{|}}{\overset{\overset{R_2}{|}}{Si}}-O\right)}_p{\left(\underset{\underset{R_7}{|}}{\overset{\overset{R_3}{|}}{Si}}-O\right)}_q\underset{\underset{R_5}{|}}{\overset{\overset{R_4}{|}}{Si}}-R_5$$

in Chemical Formula 3, $R_1$ to $R_8$ are independently an alkyl group having a carbon number of 1 to 4, or an aryl group having a carbon number of 6 to 18, Rz is an alkyl group having a carbon number of 4 to 20, and p and q are numbers which satisfy a ratio of 0.04 to 0.8:0.2 to 0.96 (p:q).

4. The composition of claim 1, wherein the vinyl siloxane comprises one or more of structures of the following Formulae 4 to 7:

[Chemical Formula 4]

$$CH_2{=}CH-\underset{\underset{CH_3}{|}}{\overset{\overset{CH_3}{|}}{Si}}-O{\left(\underset{\underset{CH_2(CH_2)_6CH_3}{|}}{\overset{\overset{CH_3}{|}}{Si}}-O\right)}_a{\left(\underset{\underset{CH_3}{|}}{\overset{\overset{CH_3}{|}}{Si}}-O\right)}_b\underset{\underset{CH_3}{|}}{\overset{\overset{CH_3}{|}}{Si}}-CH{=}CH_2$$

[Chemical Formula 5]

$$CH_2{=}CH-\underset{\underset{CH_3}{|}}{\overset{\overset{CH_3}{|}}{Si}}-O{\left(\underset{\underset{CH_2(CH_2)_2CH_3}{|}}{\overset{\overset{CH_3}{|}}{Si}}-O\right)}_a{\left(\underset{\underset{CH_3}{|}}{\overset{\overset{CH_3}{|}}{Si}}-O\right)}_b\underset{\underset{CH_3}{|}}{\overset{\overset{CH_3}{|}}{Si}}-CH{=}CH_2$$

[Chemical Formula 6]

$$CH_2{=}CH-\underset{\underset{CH_3}{|}}{\overset{\overset{CH_3}{|}}{Si}}-O{\left(\underset{\underset{CH_2(CH_2)_{10}CH_3}{|}}{\overset{\overset{CH_3}{|}}{Si}}-O\right)}_a{\left(\underset{\underset{CH_3}{|}}{\overset{\overset{CH_3}{|}}{Si}}-O\right)}_b\underset{\underset{CH_3}{|}}{\overset{\overset{CH_3}{|}}{Si}}-CH{=}CH_2$$

[Chemical Formula 7]

$$CH_2{=}CH-\underset{\underset{CH_3}{|}}{\overset{\overset{CH_3}{|}}{Si}}-O{\left(\underset{\underset{CH_2(CH_2)_6CH_3}{|}}{\overset{\overset{CH_3}{|}}{Si}}-O\right)}_a{\left(\underset{\underset{CH_3}{|}}{\overset{\overset{CH_3}{|}}{Si}}-O\right)}_b\underset{\underset{CH_3}{|}}{\overset{\overset{CH_3}{|}}{Si}}-CH_3$$

in Formulas 4 to 7, a and b are independently numbers which satisfy 0.2 to 0.5:0.5 to 0.8 (a:b).

5. The composition of claim 1, wherein the vinyl siloxane has a molecular weight of 300 to 50,000.

6. The composition of claim 1, wherein the composition comprises 100 parts by weight of vinyl siloxane including an alkyl group having a carbon number of 4 or more; and 0.001 to 10 parts by weight of a quantum dot.

7. The composition of claim 1, wherein the quantum dot has an emission peak at one or more of a wavelength of 520 to 570 nm and 620 to 670 nm.

8. The composition of claim 1, wherein the quantum dot has an emission peak at a wavelength of 570 to 620 nm.

9. The composition of claim 1, further comprising:

a fluorescent substance.

10. A composition comprising vinyl siloxane including an alkyl group having a carbon number of 4 or more and a quantum dot, wherein the composition further comprises vinyl siloxane having a structure of the following Chemical Formula 8 and including an alkyl group having a carbon number of 3 or less:

[Chemical Formula 8]

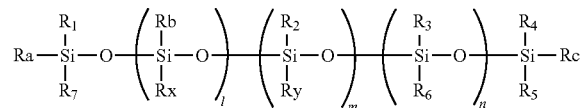

in Chemical Formula 8,

Ra, Rb, and Rc are independently an alkyl group having a carbon number of 1 to 3, a vinyl group, or an aryl group having a carbon number of 6 to 18, and one or more of Ra, Rb, and Rc are a vinyl group, $R_1$ to $R_7$ are independently an alkyl group having a carbon number of 1 to 3, or an aryl group having a carbon number of 6 to 18, Rx and Ry are independently an alkyl group having a carbon number of 1 to 3, or an aryl group having a carbon number of 6 to 18, and one or more of Rx and Ry are an alkyl group having a carbon number of 1 to 3, and l, m, and n are numbers which satisfy a ratio of 0.02 to 0.4:0.02 to 0.4:0.2 to 0.96 (l:m:n).

11. The composition of claim 10, wherein in the composition, the vinyl siloxane including an alkyl group having a carbon number of 3 or less is present in an amount of 20 to 3,000 parts by weight with respect to 100 parts by weight of the vinyl siloxane including an alkyl group having a carbon number of 4 or more.

12. A composition comprising vinyl siloxane including an alkyl group having a carbon number of 4 or more and a quantum dot, wherein a surface of the quantum dot is subjected to surface treatment with an alkyl chain having a carbon number of 6 to 30.

13. A composition comprising vinyl siloxane including an alkyl group having a carbon number of 4 or more and a quantum dot, wherein the composition further comprises a cross-linking agent and a catalyst, wherein the cross-linking agent is represented by Chemical Formula 9:

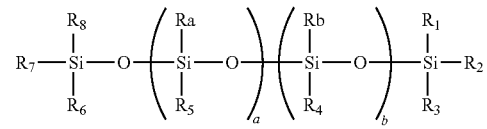

[Chemical Formula 9]

in Chemical Formula 9,

Ra and Rb are independently hydrogen, an alkyl group having a carbon number of 1 to 4, or a phenyl group, and one or more of Ra and Rb are hydrogen, $R_1$ to $R_7$ are independently an alkyl group having a carbon number of 1 to 4, or a phenyl group, and a and b are numbers which satisfy 0.002 to 0.95:0.05 to 0.998 (a:b).

14. The composition of claim 13, wherein the composition comprises 5 to 60 parts by weight of the cross-linking agent; and 0.01 to 0.5 part by weight of the catalyst, with respect to 100 parts by weight of the vinyl siloxane including an alkyl group having a carbon number of 4 or more.

15. A cured material of the composition of claim 1.

16. The cured material of claim 15, wherein the cured material is in a form of a film or a coating.

17. A device comprising the cured material of claim 15.

18. The device of claim 17, wherein the device is a lighting device, or a display device.

* * * * *

UNITED STATES PATENT AND TRADEMARK OFFICE
CERTIFICATE OF CORRECTION

PATENT NO. : 9,512,353 B2  
APPLICATION NO. : 14/374062  
DATED : December 6, 2016  
INVENTOR(S) : Doo Hyo Kwon et al.

Page 1 of 1

It is certified that error appears in the above-identified patent and that said Letters Patent is hereby corrected as shown below:

In the Claims

Column 13, Lines 50-55, delete

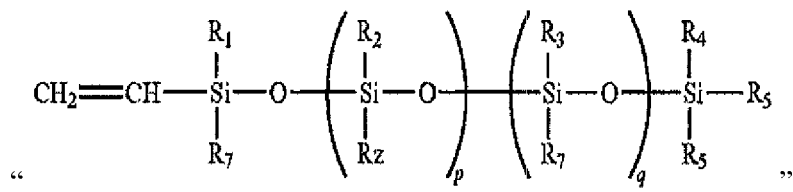

" " and insert

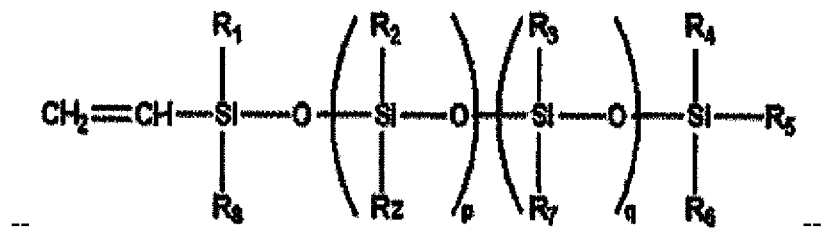

-- --

Signed and Sealed this  
Fourth Day of April, 2017

Michelle K. Lee  
*Director of the United States Patent and Trademark Office*